US00PP19229P2

(12) United States Plant Patent
Hambali

(10) Patent No.: US PP19,229 P2
(45) Date of Patent: Sep. 16, 2008

(54) ***AGLAONEMA* PLANT NAMED 'TWYAG0016'**

(50) Latin Name: *Aglaonema commutatum var. tricolor×A. rotundum hybrid*
Varietal Denomination: TWYAG0016

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/973,531

(22) Filed: Oct. 9, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Annette H Para
(74) *Attorney, Agent, or Firm*—Jondle & Associates, P.C.

(57) ABSTRACT

A new *Aglaonema* plant particularly distinguished by having a very dense leafy, compact, upright and highly branched growth habit, intermediate in stature, green and red colored leaves, very vigorous growth habit and produces numerous axillary branches and leaves, is disclosed.

1 Drawing Sheet

Genus and species: *Aglaonema commutatum* var. *tricolor×A. rotundum* hybrid
Variety denomination: 'TWYAG0016'.

BACKGROUND OF THE NEW PLANT

The present invention comprises a new and distinct cultivar of *Aglaonema,* botanically known as *Aglaonema commutatum* var. *tricolor×A. rotundum* hybrid, and hereinafter referred to by the cultivar name 'TWYAG0016'. The new cultivar originated from a hybridization made in 2000 in Bogor, Indonesia. The female parent was an unknown individual plant of *A. commutatum* var. *tricolor* (patent status unknown), while the male parent was an unknown individual plant of *A. rotundum* (patent status unknown). A single plant was selected in August 2002 for subsequent asexual propagation.

The new cultivar was created in Bogor, Indonesia and had been asexually reproduced repeatedly by vegetative cuttings and sucker division in Apopka, Fla. and Bogor, Indonesia over a 5-year period. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla. and Bogor, Indonesia.

1. Intermediate in stature;
2. Very densely leafy, compact and upright and highly branched growth habit;
3. Green and red colored leaves;
4. Vigorous growth habit; and
5. Produces numerous axillary branches and leaves.

DESCRIPTION OF THE PHOTOGRAPH

This new *Aglaonema* plant is illustrated by the accompanying photograph which shows the overall plant habit. The colors shown are as true as can be reasonably obtained by conventional photographic procedures.

DESCRIPTION OF THE NEW CULTIVAR

The following detailed description sets forth the distinctive characteristics of 'TWYAG0016'. The data which define these characteristics were collected from asexual reproductions carried out in Apopka, Fla. The plant history was taken on 18-month old plants started from a single 4-leaf rooted cutting, still in a vegetative state and grown in Apopka, Fla. Rooted cuttings were planted in 20-cm pots and grown in a greenhouse in July 2006. The average daily temperature was about 85° to 95° F. and the average nightly temperature was about 72° to 78° F. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family:*—Araceae.
- *Botanical:*—*Aglaonema commutatum* var. *tricolor×A. rotundum* hybrid.
- *Common name.*—Chinese Evergreen.

Parentage: The female parent is an unknown individual plant of *A. commutatum* var. *tricolor* (patent status unknown) and the male parent is an unknown individual plant of *A. rotundum* (patent status unknown).

Growth:
- *Form.*—Symmetrical, wider than tall; new leaves held upright while mature leaves arch outward.
- *Growth and branching habit.*—Densely leafy, compact; upright branched growth habit with basal branching; intermediate in stature.
- *Height* (*from soil to top of leaf plane*).—25 cm to 31 cm.
- *Diameter* (*area of spread, measured from leaf tip to leaf tip across the canopy*).—50 cm to 55 cm.
- *Time to produce a finished flowering plant.*—18-months starting from a single 4-leaf rooted cutting and pinched twice.
- *Vigor.*—Vigorous; plants produce numerous axillary branches and leaves.

*Growth rate.*—Somewhat more rapid than typical commercial *Aglaonema* cultivars.

*Root description.*—Abundant, fleshy white roots with finer lateral branches.

*Number of divisions or clumps per year.*—About 10 to 14, 4-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Lower temperature tolerance.*—To about 55° F. for several hours without damage.

Stems:

*Number of branches per plant.*—32.

*Length (from soil line to the junction of the newest two leaves).*—17 cm.

*Diameter (measured from the midpoint).*—0.88 cm.

*Internode length.*—1.2 cm to 1.6 cm.

*Color.*—Immature: RHS 159D and faintly mottled with RHS 144A to RHS 144C. Mature: RSH 164D tinged with RHS 144B. Oldest stems: RHS 148D mottled with RHS 146A.

*Appearance (shape).*—Columnar, cylindrical upright.

*Aspect.*—Vertical, upright.

*Strength.*—Sturdy, somewhat flexible.

*Axillary buds.*—Shape: Elliptic, flat. Length: 0.4 cm. Width: 0.19 cm. Color: RHS 155A.

Leaves:

*Arrangement.*—Alternate, single, simple, arranged in a spiral along the stem.

*Quantity of leaves per stem.*—8.

*Immature leaf (new expanded leaf).*—Color: Upper surface: Base color RHS 147A to RHS 146A suffused with coalescing spots and blotches of RHS 145C to RHS 145D and often variably tinged with RHS 48D; areas adjacent to the midrib and primary veins are marked with coalescing blotches of RHS 145C to RHS 145D and flushed with RHS 48D. Lower surface: RHS 181C base color mottled with RHS N189A to RHS 147A; areas adjacent to the primary veins and midrib marked with RHS 181C; upper surface pattern and markings visible through the lower surface.

*Mature leaf.*—Color: Upper surface: Base color darker than but closed to RHS 147A to RHS 146A suffused with coalescing spots and blotches of RHS 145C to RHS 145D and often variably tinged with RHS 48C to RHS 48D; areas adjacent to the primary veins and midrib are marked with coalescing blotches of RHS 145C to RHS 145D and flushed with RHS 49C. Lower surface: Base color RHS 181B mottled with RHS N189A to RHS 147A; areas adjacent to the primary veins and midrib marked with RHS 181B; upper surface pattern and markings visible through the lower surface.

*Length.*—15.0 cm to 17.5 cm.

*Width.*—General: The leaf blade folds upward along the midrib. Flattened: 6.5 cm to 9.2 cm. Not flattened: 5.0 cm to 7.0 cm.

*Shape.*—Elliptic.

*Apex.*—Acuminate.

*Base.*—Acute to obtuse.

*Margin.*—Smooth, entire, mostly flat with some broad undulations.

*Texture.*—Smooth; immature leaves glossy to shiny; mature leaves glossy; the leaf blades is convex between the main veins resulting in a textured appearance.

*Pubescence.*—None.

*Venation pattern.*—Pinnate, radiating outward form the midrib in a herringbone arrangement.

*Venation color (immature leaf).*—Upper surface: Primary veins: RHS 50C. Midrib: RHS 48D with streaks of RHS 48B and RHS 146C. Lower surface: Primary veins: RHS 49C. Midrib: RHS 51C.

*Venation color (mature leaf).*—Upper surface: Primary veins: RHS 50C with steaks of RHS 50B Midrib: RHS 50C to RHS 50D with streaks of RHS 50B and RHS 146C. Lower surface: Primary veins: RHS 49B to RHS 49C. Midrib: RHS 51C.

*Petioles.*—Aspect: Vertical upright when newly expanded, becoming curved outward and about 45° with maturity. Length: 8.5 cm. Diameter: Distal: 0.4 cm. Proximal (petiole and petiole sheath clasps the stem proximally): Flattened: 2.0 cm. Natural diameter: 0.9 cm. Color: Distal: RHS 51C tinged with RHS 51B (between the top of the wing and the base of the leaf). Proximal: RHS 50C. Area adjacent to stem: RHS 36D. Wing length: 4.8 cm. Wing diameter: Mid-point: 0.7 cm. Base: 0.9 cm. Depth: 0.65 cm. Wing color: Inside: RHS 49D streaked with RHS 50D. Outside: RHS 49C to RHS 49D streaked with RHS 50C to RHS 50D. Area adjacent to stem: RHS 36D.

Inflorescence: None observed.

Fruit and seed set: None observed.

Disease and insect resistance: Typical of *Aglaonema;* no particular susceptibility or resistance to pests or diseases noted.

COMPARISON WITH PARENTAL AND COMMERCIAL CULTIVARS

'TWYAG0016' differs from the female parent an unknown individual plant of *A. commutatum* var. *tricolor* in that 'TWYAG0016' has elliptical shaped leaves, while the female parent has leaves that are elliptical to oblong. 'TWYAG0016' has leaves with a reddish-green lower surface, while the female parent has leaves with a pale yellowish-green color on the lower surface. In addition, the petioles of 'TWYAG0016' are dark-pink, while the female parent has petioles that are light-pink.

'TWYAG0016' differs from the male parent an unknown individual plant of *A. rotundum* in that 'TWYAG0016' has elliptical shaped leaves, while the male parent has leaves that are ovate. 'TWYAG0016' has leaves with a reddish-green lower surface, while the male parent has a dark-purple or maroon color on the lower surface of the leaves. In addition, the petioles of 'TWYAG0016' are dark-pink, while the male parent has petioles that are green.

'TWYAG0016' differs from the commercial variety 'Red Gold' (unpatented) in that 'TWYAG0016' has elliptical shaped leaves, while the 'Red Gold' has leaves that are broadly ovate to elliptical. 'TWYAG0016' has leaves with a reddish-green lower surface, while 'Red Gold' has leaves with a pale yellowish-green color on the lower surface. In addition, the petioles of 'TWYAG0016' are dark-pink, while 'Red Gold' has petioles that are creamy-yellow.

I claim:

1. A new and distinct cultivar of *Aglaonema* plant as shown and described herein.

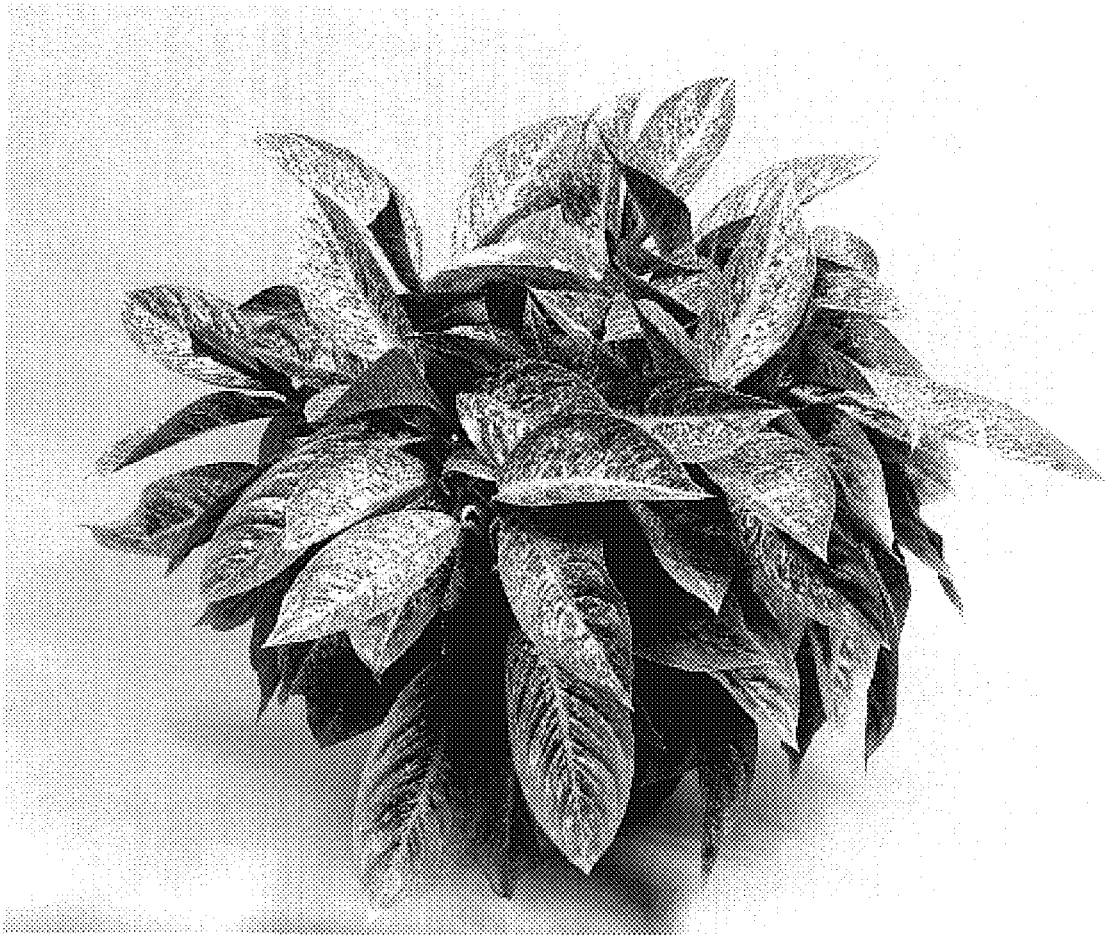

* * * * *